United States Patent [19]

Fujiwhara et al.

[11] 3,958,993
[45] May 25, 1976

[54] DEVELOPMENT INHIBITOR-RELEASING TYPE COMPOUND FOR PHOTOGRAPHIC USE

[75] Inventors: Mitsuto Fujiwhara; Takaya Endo; Ryosuke Satoh; Toyoaki Masukawa; Satoshi Nakagawa, all of Hino, Japan

[73] Assignee: Konishiroku Photo Industry Co., Ltd., Tokyo, Japan

[22] Filed: Nov. 23, 1973

[21] Appl. No.: 418,589

[30] Foreign Application Priority Data
Nov. 29, 1972 Japan............... 47-118892

[52] U.S. Cl..................... 96/66.3; 96/3; 96/95
[51] Int. Cl.²......................... G03C 5/30
[58] Field of Search .............. 96/3, 29 D, 66.3, 95

[56] References Cited
UNITED STATES PATENTS

| | | | |
|---|---|---|---|
| 3,364,022 | 1/1968 | Barr | 96/66.3 |
| 3,379,529 | 4/1968 | Porter et al. | 96/66.3 |

Primary Examiner—David Klein
Assistant Examiner—Judson R. Hightower
Attorney, Agent, or Firm—Jordan B. Bierman; Linda Bierman; Kenneth J. Stempler

[57] ABSTRACT

A silver photosensitive material comprising a development inhibitor-releasing compound of the formula

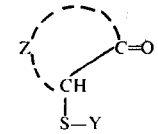

wherein Z is an atomic group necessary to form a 5 to 7 membered saturated or unsaturated carbon ring with the carbon atoms to which it is attached, said ring being unsubstituted or substituted by at least one of halogen and a member of the class consisting of alkyl, aryl, alkoxy, acyloxy, aryloxy, SY and a group forming a condensed carbon ring with said saturated or unsaturated carbon ring; Y is arylmercapto, heterocyclic, thioglycollic acid, cystein or glutathione. A method for the development of silver halide photosensitive material by the use of the foregoing compound is also disclosed.

4 Claims, No Drawings

DEVELOPMENT INHIBITOR-RELEASING TYPE COMPOUND FOR PHOTOGRAPHIC USE

This invention relates to a development inhibitor-releasing type compound for photographic use. It is known that a compound capable of releasing a development inhibiting agent in correspondence to the density of an image (hereinafter referred to as a "development inhibitor-releasing type compound") is incorporated into a silver halide photosensitive material. In general, a compound of this type reacts with the oxidized-color developing agent and then releases a development inhibitor. As a typical instance of such compound, there is known a so called DIR coupler, in which a group capable of forming a compound having a development inhibiting activity when it is released from the coupler is introduced to the coupling position.

In this DIR coupler, when it is coupled with the oxidized color developing agent the coupler forms a dye and simultaneously releases a development inhibitor.

In general, development inhibitor-releasing type compounds are employed for the following purpose. The development inhibitor-releasing type compound is characterized in that it releases a development inhibitor in correspondence to the density of an image during development. The so released development inhibitor inhibits the development depending on the image density in an emulsion of the photosensitive material, whereby control of the image tone, reduction of the image grain size of silver crystals forming image and improvement of the image sharpenss, namely, a so called intra-image effect, can be attained. On the other hand, when the development inhibitor diffuses to other layers, the development of that layers is controlled depending on the image density of the layers containing the development in inhibitor-releasing type compound, namely it exhibts a so called masking effect, and in the case of mono-color exposure or the like, it improves quality of the color image by inhibition of the development in other layer.

Thus, the development inhibitor exhibts so called interimage effects. In short, the development inhibitor-releasing type compound is expected to exhibit the foregoing two kinds of image effects.

Various development inhibitor-releasing type compounds have heretofore been known in the art. However, none of them satisfies the above expectation sufficiently. For instance, when the development inhibitor-releasing type compound which forms a dye on the color development is employed, opaqueness appears on an image unless care is taken in selection of this dye, and on the other hand, if this dye is appropriately chosen, it sometimes happens that a desired inhibiting effect cannot be obtained or it is not at all suitable for certain kinds of silver halide photosensitive materials. Further, development of inhibitor-releasing compounds that do not form a dye are defective in that they should be used in large amounts because of poor reactivity with the color developing agent. This fact causes to degrade the photographic characteristics such as sensitivity and also to degrade the stability. Further, in case such compounds are used in small amounts, sufficient effects cannot be obtained.

This invention is based on the finding that when a certain kind of a specific compound is used as the development inhibitor-releasing type compound, the above mentioned defects of the conventional compounds can be overcome and it exhibits excellent intra-image and inter-image effects, with the result that an image of excellent quality can be obtained.

The development inhibitor-releasing type compound to be used in this invention forms a substantially colorless compound and releases a development inhibitor upon reaction with the oxidation product of the color developing agent. Such compounds to be used in this invention are represented by the following gneral formula:

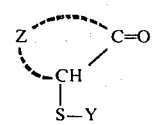

(wherein Z stands for an atomic group necessary for formation of a carbon ring, and Y designates a group forming a compound having a development-inhibiting activity together with the sulfur atom of the thioether linkage when it is released therefrom).

Since a compound of this type forms a colorless compound upon reaction with the oxidation product of the color developing agent and the so formed colorless compound does not constitute a part of the final image, the kind of the compound to be used need not be changed depending on the kind of the layer to which the compound is applied and one compound can be applied to any layer and any photgraphic material. This is one of advantages of the development inhibitor-releasing type compound of this invention. Further, since the compound of this invention has a very high reactivity with the color developing agent, even when it is used in a very samll amount, excellent intra-image and inter-image effects can be obtained. This is another advantage of the development inhibitor-releasing type compound of this invention. Still further, either a diffusing development inhibitor or a non-diffusing development inhibitor can be fully chosen by selecting appropriately the kind of the carbon ring or the kind of the substitutent thereof in the development inhibitor-releasing type compound. Therefore, a suitable compound can easily be chosen depending on the intended application object. This is still another advantage. For instance, a diffusing inhibitor-releasing compound can be incorporated in any of constituent layers of a photosensitive material for color photography, and in some extreme case, it is possible to obtain the intended effects in all the layers of a photosensitive material for color photography, and in some extreme case, it is possible to obtain the intended effects in all the layers of a photosensitive material by incorporating it merely in one layer. Further, by adjusting the diffusibility of the development inhibitor in the incorporated layer it is made possible to form a gradient of the activity of the inhibitor in other layers. Furthermore, a diffusing inhibitor-releasing compound can also be incorporated in a color developer.

In the case of a non-diffusing inhibitor-releasing compound, good results are obtained when it is desired that both the intra-image and inter-image effects are attained only in one specific layer. Further, when a certain ingredient of the activity of the development inhibitor is desired to be formed among layers of the photosensitive material, this object can readily be attained by changing the concentration of the compound among the layers of the photosensitive material.

Typical instances of compounds represented by the above general formula will now be described. Z in the formula indicates, for instance, a 5-, 6- or 7-membered saturated or unsaturated carbon rings. Typical instances of the carbon ring Z includes cyclopentanone, cyclohexanone, cyclohexenone and the like, and they may comprise at least one substituent selected from alkyl groups, aryl groups, alkoxy groups, aryloxy groups, halogen atoms and the like.

Further, they include carbon rings containing a condensed ring at a suitable position, and as typical instances of such condensed ring, there can be mentioned indanone, benzcyclohexenone, benzcyclohexanone, etc. Still further, such carbon ring can contain at least one —SY group (in which Y is as defined above). The group Y in the above general formula designates a group forming together with the sulfur atom of the thioether group when the atom is released therefrom, a compound having a development inhibiting activity, such as arylmercapto compounds, heterocyclic compounds, thioglycol acid type compounds, and cystein and glutathione derivatives. As typical instances of mercapto compounds formed by the group Y are mercapto-tetrazole compounds such as 1-phenyl-2-mercaptotetrazole, 1-nitrophenyl-5-mercaptotetrazole and 1-naphthyl-5-mercaptotetrazole; mercaptothiazole compounds such as 2-mercaptobenzthiazole and mercaptonaphthothiazoel; mercaptooxadiazole compounds; mercaptopiperidine compounds; mercaptothiadiazole compounds such as 2-mercaptothiadiazolotriazine; mercaptotriazine; mercaptotriazole compounds, mercaptobenzene compounds such as 1-mercapto-2-benzoic acid, 1-mcrapto-2-nitrobenzene and 1-mercapto-3-hepta-decanoylaminobenzene, and the like. As specific instances of the compound represented by the above general formula, the following compounds can be mentioned;

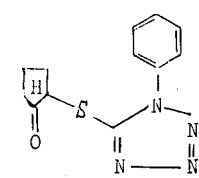

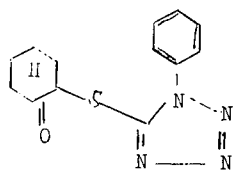

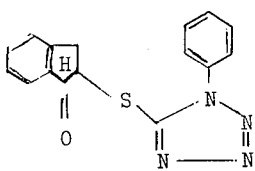

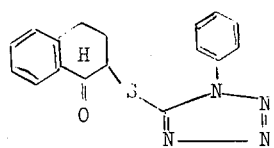

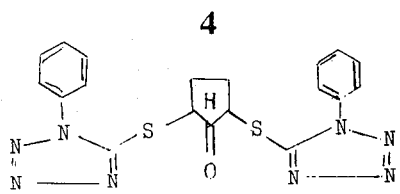

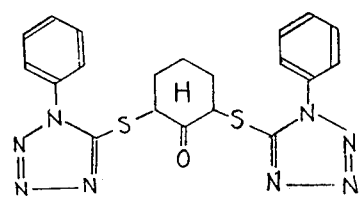

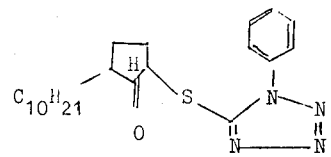

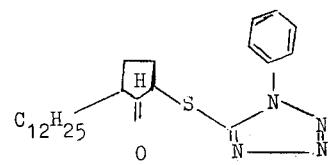

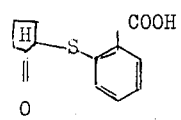

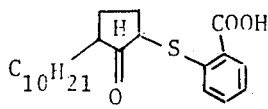

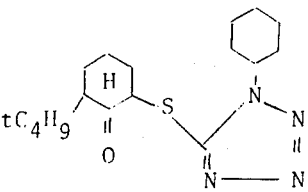

5
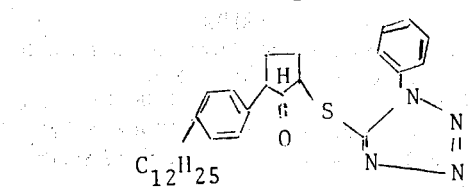
6
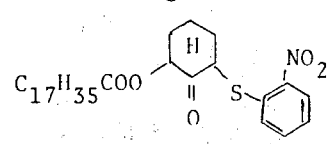
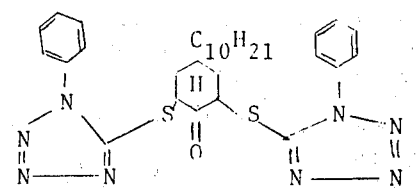
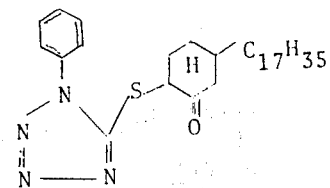
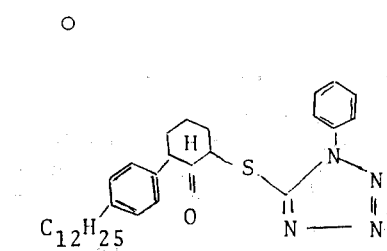
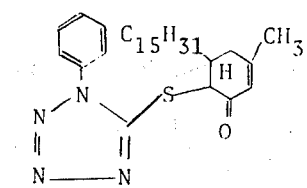
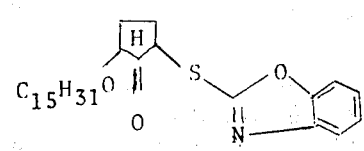
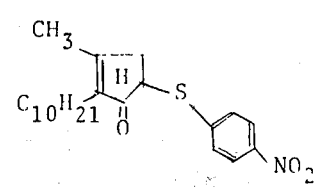
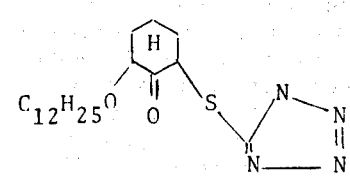
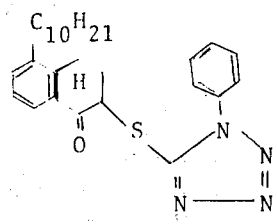
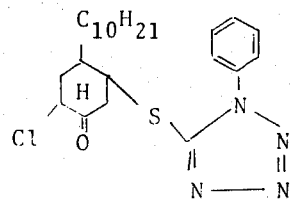
23
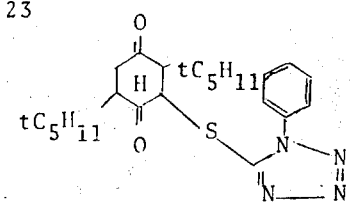

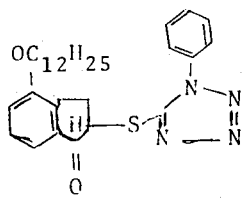

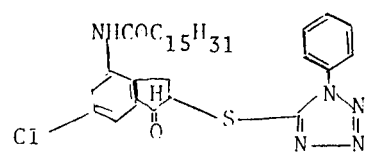

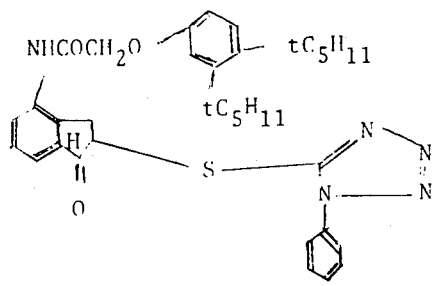

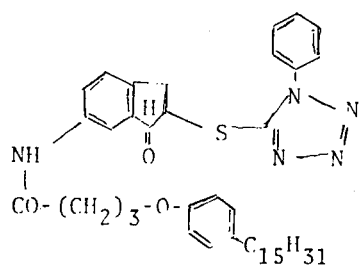

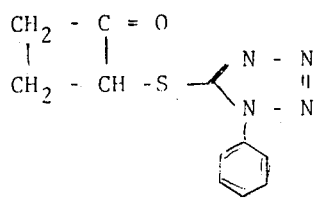

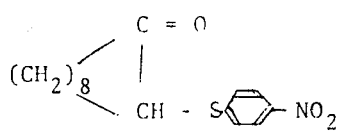

Typical instances of the method for synthesis of these compounds represented by the above general formula will now be illustrated by reference to Synthesis Examples. Compounds other than those described in these Synthesis Examples can be synthesized according to methods similar to methods described in these Synthesis Examples.

Synthesis Example 1

Synthesis of Compound (2):

27 g of 2-chlorocyclohexanone-1 and 40 g of sodium 1-phenyl-5-mercaptotetrazole were heated and refluxed for 20 minutes in 50 ml of acetone, and after cooling, sodium chloride formed by the reaction was removed by filtration and the filtrate was concentrated. From the oily residue was removed a minute amount of remaining, unreacted 1-phenyl-5-mercaptotetrazole by column chromatography, and 45 g of an oily product was obtained. As a result of the nuclear magnetic resonance spectrum, the IR absorption spectrum and the elementary analysis the product was identified as compound (2).

Synthesis Example 2

Synthesis of Compound (5):

10 g of cyclopentanone was added to 100 ml of carbon tetrachloride, and solution of 50.6 g of 1-phenyl-5-tetrazolylsulfenyl chloride in 200 ml of carbon tetrachloride was added to the above liquid mixture. The resulting mixture was agitated at room temperature for 1 hour and then concentrated. The remaining oily product was heated and dissolved in 200 ml of benzene, and the solution was allowed to stand still to precipitate crystals. After filtration, the crystals were recrystallized from a mixed solvent of acetonitrile and alcohol to obtain 25 g of a white solid melting at 124° to 127°C.

Synthesis Examples 3

Synthesis of Compound (7):

22.4 g of 2-decylcyclopentanone-1 was added to 80 ml of carbon tetrachloride and the mixture was cooled from the outside by the use of an ice bath. Then, a solution of 24.0 g of 1-phenyl-5-tetrazolylsulfenyl chloride in 100 ml of carbon tetrachloride was added to the above liquid under agitation. The resulting mixture was agitated for 1.5 hours. The mixture was concentrated and the remaining sulfide or 1-phenyl-2-mercaptotetrazole was removed from the residual oily product by column chromatography to obtain 30.5 g of an oily product. As a result of the nuclear magnetic resonance spectrum, the IR absorption spectrum and the elementary analysis, the product was identified as compound (7). Other compounds represented by the above general formula can be synthesized according to a method similar to those described in Synthesis Examples. Data of the analysis value of sulfur in compounds (1) to (22) are given below:

| Compound No. | Molecular Formula | Elementary Analysis (sulfur) calculated | found |
|---|---|---|---|
| (1) | $C_{12}H_{12}N_4OS$ | 12.32 | 12.59 |
| (2) | $C_{16}H_{14}N_4OS$ | 9.59 | 10.01 |
| (3) | $C_{16}H_{12}N_4OS$ | 10.40 | 10.49 |
| (4) | $C_{17}H_{14}N_4OS$ | 9.95 | 10.01 |
| (5) | $C_{19}H_{16}N_8OS_2$ | 14.69 | 14.42 |
| (6) | $C_{20}H_{18}N_8OS_2$ | 14.29 | 14.14 |

-continued

| Compound No. | Molecular Formula | Elementary Analysis (sulfur) calculated | found |
|---|---|---|---|
| (7) | $C_{22}H_{32}N_4OS$ | 8.00 | 8.30 |
| (8) | $C_{24}H_{36}N_4OS$ | 7.48 | 7.65 |
| (9) | $C_{12}H_{12}OS$ | 13.48 | 13.71 |
| (10) | $C_{22}H_{32}O_3S$ | 8.52 | 8.53 |
| (11) | $C_{30}H_{40}N_4OS$ | 6.35 | 6.34 |
| (12) | $C_{17}H_{22}N_4OS$ | 9.70 | 9.85 |
| (13) | $C_{30}H_{33}N_8OS_2$ | 10.85 | 10.60 |
| (14) | $C_{31}H_{42}N_4OS$ | 6.18 | 6.26 |
| (15) | $C_{27}H_{41}NO_3S$ | 6.98 | 6.98 |
| (16) | $C_{25}H_{38}N_4O_2S$ | 6.99 | 7.03 |
| (17) | $C_{30}H_{47}NO_5$ | 6.01 | 6.21 |
| (18) | $C_{30}H_{46}N_4OS$ | 6.28 | 6.29 |
| (19) | $C_{29}H_{44}N_4OS$ | 6.45 | 6.60 |
| (20) | $C_{22}H_{31}NO_3S$ | 8.23 | 8.11 |
| (21) | $C_{28}H_{38}N_4OS$ | 6.70 | 6.48 |
| (22) | $C_{23}H_{33}ClN_4OS$ | 7.14 | 7.30 |
| (23) | $C_{23}H_{20}N_4O_2S$ | 7.70 | 7.62 |
| (24) | $C_{28}H_{36}N_4O_2S$ | 6.51 | 6.78 |
| (25) | $C_{32}H_{42}ClN_5O_2S$ | 5.38 | 5.62 |
| (26) | $C_{34}H_{35}N_5O_3S$ | 5.36 | 5.84 |
| (27) | $C_{41}H_{53}N_5O_3S$ | 4.61 | 4.96 |
| (28) | $C_{11}H_{10}N_4OS$ | 13.02 | 13.07 |
| (29) | $C_6H_{21}NO_3S$ | 10.43 | 10.59 |

Compounds represented by the above general formula, which are synthesized according to methods such as described above, can be used for various silver halide, photosensitive materials such as those for Black and White photography and the like. More specifically, they can be applied to various silver halide photosensitive materials for use in ordinary Black and White graphy, ordinary printing, X-ray photography, electron photography, high resolving power monochromatic photography, color photophotography, color X-ray photography, diffusion transfer type color photography and the like.

As the silver halide to be used in these photographic materials, there can be mentioned silver chloride, silver bromide, silver iodide and mixed silver halides such as silver chlorobromide, silver iodobromide and silver chloro-iodo-bromide. These silver halides can be prepared by various methods, and they are used in the form of a so called conversion emulsion, a Lippmann emulsion or the like and a suitable form is chosen depending on the kind of the photosensitive material.

Further, the particle size, content and mixing ratio of the silver halide is varied on the kind of the photosensitive material. In genral, silver chloride is used as the main component in the case of an emulsion having a relatively low sensitivity and having a finer grain size, and in the case of an emulsion having a relatively high sensitivity, the content of silver chloride is reduced. In the case of a direct reversal photosensitive material, an optical or chemical fog is given to the silver halide. It is known the active gelatin, sulfur sensitizers such as allylthiocarbamide, thiourea and cystine, selenium sensitizers, noble metal sensitizers such as gold sensitizers, e.g., potassium chloroaurite, potassium aurithiocyanate, potoassium chloroaurate and 2-aurosulfobenzothiazole methochloride, and such sensitizers as ruthenium, rhodium, palladium and iridium salts act as sensitizers or fog inhibitors to such silver halides depending on amounts incorporated of such sensitizers. The silver halide to be used in this invention can be chemically sensitized with use of one or more of these sensitizers.

This silver halide can be coated in the form of a layer on a support by vacuum evaporation deposition or the like without use of a binder, or a so called silver halide emulsion prepared by dispersing the silver halide in a binder composed of one or more of gelatin, other colloidal substances such as colloidal albumin, cellulose derivatives and synthetic resins such as polyvinyl compounds is applied in the form of a layer on a support, if necessary, through an undercoat layer, intermediate layer and the like. Such silver halide emulsion can be optically sensitized by a cyanine a merocyanine dye or the like. For instance, in a photosensitive material for color photography, three different sensitive silver halide emulsions are employed. This silver halide emulsion can be stabilized by a triazole, an azaindene, a quaternary benzothiazolium compound or a zinc or cadmium compound, and it can comprise a sensitizing compound of the qaternary ammonium salt or polyethylene glycol type. It may further comprise a suitable gelatin plasticizer such as glycerin, a dihydroxyalkane, e.g., 1,5-pentane diol, esters of ethylene-bis-glycolic acid, bis-ethoxydiethylene glycol succinate, amides of the acrylic acid type, latex and the like; a gelatin hardening agent such as formaldehyde, a halogen-substituted fatty acid, e.g., mucobromic acid, and acid anhydride group-containing compound, a dicarboxylic acid chloride, a diester of methanesulfonic acid and a sodium bisulfite derivative of a dialdehyde in which the aldehyde groups are separated by 2 to 3 carbon atoms; an extender such as saponin; a coating such as a salt of sulfosuccinic acid; other various photographic additives.

Especially in the case of a photosensitive material for the coupler incorporated-type color photography, a coupler such as a magenta coupler of the 5-pyrazolone type, a coupler of the open-chain ketomethylene type and yellow coupler of the open-chain ketomethylene type may be contained in the silver halide emulsion. Such coupler may be either a so called two-equivalent coupler or a four-equivalent coupler, or it may be a so called masking coupler having, for instance, an arylazo group at the coupling position. In this case, it is desired that a so called colorless coupler which is colorless such as mentioned above are employed in combination.

Further, in the case of a so called protective type coupler, coupler solvent may be contained as a coupler dispersing agent. Still further, the silver haldie emulsion can contain a so called competing coupler together with a variety of couplers, whereby photographic characteristics can be improved. In the case of a photographic material for diffusion transfer color photography, a dye developer or a coupler developer can be incorporated instead of such coupler. As the dye developer, there are employed compounds having an activity as a dye and an activity as a developer in combination, for instance, a compound formed by introducing hydroquinone or an aromatic primary amine color developing agent into a dye molecule. As the coupler developer, there are employed compounds having an activity as the coupler and an activity as the developer, for instance, a compound formed by introducing hydroquinone or the like into coupling position of a coupler such as mentioned above or other points.

Furthermore, in the case of a photosensitive material for color photography to be used in the silver dye bleaching method, a dye may be incorporated in advance in the photographic material. More over, ultraviolet absorbers, fluorescent whitening agents and the like may be incorporated in a photographic silver halide emulsion for color photography or the like.

Such silver halide emulsion is applied in the form of a layer on a support, if necessary, through an undercoat layer and an intermediate layer to form a silver halide photosensitive material. As the support, there are employed, for instance, films or sheets of paper, laminated paper, glass, cellulose acetate, cellulose nitrate, films and sheets of polyesters, polyamides and polystyrene, and glass plate. A suitable support is chosen appropriately depending on the intended use of the photosensitive material. In principle, the photosensitive material is composed of support and photosensitive layer (silver halide vacuum deposited layer or silver halide emulsion layer). As mentioned above, in some kind of photosensitive materials a multi-layer structure including an undercoat layer, an intermediate layer, a filter layer a curl-preventive layer, a protective layer and the like is formed. Further, the photosensitive layer per se may have a plurality of layers differing in the sensitivity in the same or different wavelength regions. Each of these layers may contain various photographic additives such as the above mentioned additives to be incorporated in the silver halide emulsion, and peculiar additives are incorporated in respective layers, for instance, a filter dye into the filter layer and a film property-improving agent into the protective layer. Still further, an intermediate layer containing a physical development nucleus may be formed in the diffusion transfer photographic photosensitive material or the like.

When such silver halide photosensitive material is developed in the presence of a compound represented by the above general formula, such excellent photographic characteristics as mentioned above can be obtained. As one embodiment there can be mentioned a method in which such compound is incorporated in a photosensitive material and then developed.

In this embodiment, if the compound has a diffusing property, it may be incorporated in any layer of the photosensitive material, for instance, in one or more of the emulsion layer, the intermediate layer, the protective layer and the like. In the case of a non-diffusing compound, it is desired that the compound is incorporated in the emulsion layer and one or more layers adjacent to the emulsion layer. When such compound is incorporated into the photosensitive material, it may be contained in various forms into a coating liquid to be used for formation of a structural layer into which the compound is to be incorporated. For instance, a diffusing type compound is added in the form of a solution and a non-diffusing type compound is added in the form of an emulsion. More specifically, the diffusing type compound is incorporated in the form of an alkali aqueous solution and the non-diffusing type compound is incorporated in the form of an emulsion in a solvent for such couplers as mentioned above. In general, as the coupler solvent there are employed, for instance, water-immiscible high boiling point organic solvents such as di-n-butyl phthalate, benzyl phthalate, tri-phenyl phosphate, tri-o-cresyl phosphate monophenyl-di-p-t-butylphenyl phosphate and the like. Further, these high boiling point organic solvents can be combined with low boiling point organic solvents such, as methylisobutylketone, β-ethoxyethyl acetate, methoxytriglycol acetate, acetone, methylacetone, methanol, ethanol, acetonitrile, dioxane, dimethyl-formamide, ethyl acetate, isopropyl acetate, chloroform and the like. Moreover, these low boiling point organic solvents can be used instead of high boiling point solvents.

These organic solvents can be used singly or in the form of a mixture of two or more of them. In another embodiment of this invention, for instance, photosensitive material for a diffusion transfer process comprising such an image receiving material is developed in such state that both of the materials are contacted closely to each other. In this embodiment, a compound represented by the above general formula can be incorporated into said another photographic material, and although it is desired that the compound to be used is diffusible in come cases where the image-receiving material is an image-receiving layer (for example, a gelatin layer, a polyvinyl compound layer or the like.) formed on the support, in which silver halide particles having a physical development nucleus are incorporated, non-diffusing type compounds can be employed. According to still another embodiment of this invention, when a compound of the above general formula is contained in the photographic material or another photographic material such as an iamge-receiving material, if the compound has a special substituent, a carrier such as mordant is incorporated into a specific layer to protect said compound while such protection is required. For instance, a compound having an anionic group is protected by an amino group or the like contained in a certain kind of a mordant, and the protected anionic group is made free at the time of development.

According to a still further embodiment of this invention, a compound of the above gneral formula may be incorporated in a developer or pre-treating liquid. As such developer or pre-treating liquid to be used for such purpose, a developer for monochromatic photography, a color developer, e.g., a developer for color photographic process of the coupler incorporated type or the coupler non-incorporated type, either or both of first and second developers to be used in reversal develpment, an ordinary black and white developer, a developer for X-ray photography, and a pre-treating solution such as film-hardener. In general, a diffusible type is preferably used as the compound of the above general formula in the above developer or pre-treating solutions.

Further, it is possible to emphasize the effect in some specific layer of the photosensitive material by incorporating in advance a carrier in said specific layer.

In the foregoing embodiments, it is desired that an aromatic primary amine is made present as the color developing agent.

As mentioned above, compounds of this invention can be used in various embodiments, and they give more excellent image effects than conventional development inhibitor-releasing type compounds, and the effects are especially conspicuous in the embodiment where these compounds are incorporated in a photosensitive material. The amount used of the compound represented by the above general formula is greatly changed depending on the application method, the object of application, the intended effects and other factors, but it is generally preferred that the compound is used in an amount of 0.1 to 10 g per Kg of the silver halide emulsion. In case the compound is used in such a large amount as in the case of conventional development inhibitor-releasing type compound, much higher effects can be obtained, and if image effects similar to those attained by the conventional compounds are desired, the amount used of the compound of the above general formula can be greatly reduced.

In case that the compound of the above general formula is added to a treating liquid such as developer, the following composition can be used as coupler incorporated developer:

| | |
|---|---|
| color developing agent | 2 to 8 g |
| anhydrous sodium sulfite | 1.0 to 6 g |
| sodium carbonate monohydrate | 40 to 100g |
| potassium bromide | 0.5 to 2 g |
| coupler | 0.002 to 0.01 mole |
| compound of the above general formula | 1.0 to 5.0 g |
| water | balance |
| TOTAL | 1 liter |

When the coupler is removed from the above composition, a typical instance of the composition of the color developer in color photographic process of the coupler incarporated type is obtained. In each developer, the pH value is adjusted and other various photographic additives can be employed. A more specific instance of the composition of the color developer in color photographic process of the coupler non-incorporated type is as follows:

| | |
|---|---|
| N-ethyl-N-β-methanesulfoneamido-ethyl-3-methyl-4-aminoaniline | 5.0 g |
| sodium sulfite | 2.0 g |
| benzyl alcohol | 3.5 ml |
| sodium carbonate | 82 g |
| potassium bromide | 1.0 g |
| coupler | 0.05 mole |
| compound of the above general formula | 2.0 g |
| water | balance |
| TOTAL | 1 liter |

A more specific instance of the composition of the color developer in color photographic process of the coupler incorporated type is as follows:

| | |
|---|---|
| N-ethyl-N-β-methanesulfonamido-3-methyl-4-aminoaniline sulfate | 5.0 g |
| anhydrous sodium sulfite | 2.0 g |
| benzyl alcohol | 3.8 g |
| sodium carbonate monohydrate | 50 g |
| potassium bromide | 1.0 g |
| potassium hydroxide | 0.55 g |
| compound of the above general formula | 2.5 g |
| water | balance |
| TOTAL | 1 liter |

In this invention, it is preferred that the color developing agent is selected from aromatic primary amino compounds, especially p-phenylene diamine type compounds such, as N,N-diethyl-p-phenylene diamine, N-ethyl-N-ω-sulfobutyl-p-phenylene diamine, 2-amino-5-diethylaminotoluene, p-amino-N-ethyl-N -β-hydroxyethylanilin and the like. It is desired that at the step of the development treatment of the photosensitive material the compound of the above general formula is made co-present with one or more of such color developing agents. Further, it is also possible to employ two or more of compounds of the above general formula for practice of the method of this invention. As a typical instance of such method, there can be mentioned an embodiment in which a non-diffusing type, development inhibitor-releasing compound is incorporated in a specific layer of the lightsensitive photographic material and a diffusing type, development inhibitor-releasing compound is incorporated in a treating liquid, and such light-sensitive material is treated with such treating liquid. The photographic material thus treated according to the development treatment method of this invention is post-treated with treating liquids for ordinary photographic treatments, such as a stopper containing an organic acid, a stop fixing liquid comprising an organic acid and hypo or ammonium thiosulfate as the fixing agent a bleaching liquid containing as main ingredients a ferric salt of an aminopolycarboxylic acid and an alkali halide, a bleach fixing liquid containing a ferric salt of an aminopolycarboxylic acid and hypo or ammonium thiosulfate as the fixing agent, and a stabilizing liquid, and is subjected to the water washing treatment and the drying treatment. These post treatment are conducted in combination appropriately depending on the photosensitive material used. This invention will now be illustrated more detailedly by reference to Examples, which by no means limit the scope of this invention or embodiments of this invention.

Example 1

Samples I and II were prepared in the following manner.
Sample I:
2 g of compound (7) and 15 g of a magenta coupler, 1-(2,4,6-trichlorophenyl)-3-(3-(2,4-di-tert-amyl-phenoxyacetamido) benzamino)-5-pyrazolone, were dissolved in 30 ml of ethyl acetate and 15 ml of dibutyl phthalate, and the solution was mixed with 20 ml of a 10% aqueous solution of Alkanol B (manufactured by Du Pont) and 260 ml of a 5% aqueous solution of gelatin and the mixture was emulsified and dispersed by means of a colloid mill. Then, the resulting dispersion was added to 1 Kg of a green-sensitive silver iodobromide emulsion and dispersed therein.

The resulting dispersion was coated on a cellulose triacetate base and dried.

Sample II

As comparative sample, another sample was prepared by the same procedures as above except that compound (7) was not added.

These samples I and II were subjected to wedge exposure, developed with a liquid developer having the following composition, and bleached and fixed according to customary treatment methods:

| | |
|---|---|
| N,N-dimethyl-p-phenylene diamine hydrochloride | 2.0 g |
| anhydrous sodium sulfite | 2.0 g |
| sodium carbonate monohydrate | 82.0 g |
| potassium bromide | 2.0 g |
| water | balances |
| TOTAL | 1 liter |

In each sample an image composed of a magenta dye was formed. The sensitivity was at the same level in each sample, but value was 0.9 in sample II and 0.5 in sample I. The magenta dye image of sample II was composed of much finer particles than in sample I.

Example 2

Samples III and IV were prepared in the following manner.
Sample III:
2 g of compounds (7) and 15 g of a magenta coupler 1-(2,4,6-trichlorophenyl)- 3-(2,4,-di-tert-amyl-phenoxy) acetamido benzamido-5-pyrazolone, were dissolved in 30 ml of ethyl acetate and 15 ml of dibutyl phthalate, and the solution was mixed with 20 ml of a 10 % aqueous solution of Alkanol B and 200 ml of a 5% aqueous solution of gelatin and the mixture was emulsified and dispersed by means of a colloid mill. The resulting dispersion was added to 1 Kg of a green-sensitive silver iodobromide emulsion and dispersed therein.

The resulting dispersion was coated on a cellulose triacetate base and dried

Sample IV:

Another sample was prepared in the same manner as above except that 7.2 g (molar amount three times the molar amount of compound (7) used for formation of sample III) of p-lauroylamido-ω-(1-phenyl-5-tetrazolylthio) acetophenone(comparative compound) was employed instead of compound (7).

Each sample was exposed to light and treated in the same manner as in Example 1. Results are as follows:

|  | Sensitivity | γ value |
|---|---|---|
| Sample III | 97 | 0.5 |
| Sample IV | 98 | 0.65 |

As is seen from the above results, the sensitivity was as the same level in both the samples, and in sample III the value was lowered even if the amount of compound (7) was one-third of the amount used of the comparative compound. Further, the compound (7) of this invention was superior to the comparative compound with respect to the graininess and sharpness of the resulting magenta dye image. The comparative compound used in this Example is a development inhibitor-releasing type compound disclosed in Patent Publication No. 22514/67.

Example 3

Samples V and VI were prepared in the following manner.

Sample V:

15 g of 2-[α-(2,4-di-tert-amylphenoxy)butylamido]-4, 6-dichloro-5-methylphenol was added to 1 kg of a red-sensitive silver iodobromide emulsion, and the emulsion was coated on a cellulose triacetate base. A green-sensitive silver halide emulsion containing 3 g of compound (12) and 20 g of 1-(2,4,6-trichlorophenyl)-3-{3-[α-(2,4-di-tert-amylphenoxy)acetamido]benzamido}-5-pyrazolone was coated on the above red-sensitive emulsion layer and dried.

Sample VI:

A comparative sample was prepared in the same manner as above except that the green-sensitive emulsion layer contained the magenta coupler but did not contain compound (12) of this invention.

Both the samples V and VI were subjected to red light wedge exposure and white light wedge exposure, developed with the same liquid developer as used in Example 1, and bleached and fixed according to customary procedures. In the case of sample V, the γ value was at the same level in either the cyan dye image obtained by white light exposure or the cyan dye image obtained by red light exposure, but in the case of sample VI the γ value of the cyan dye image obtained by white light exposure was apparently lower than the γ value of the cyan dye image obtained by red light exposure. In the sample V, the development inhibitor released from compound (12) by white light exposure diffused to the red-sensitive layer to inhibit the development in the red-sensitive layer, which resulted in reduction of the γ value in the red-sensitive layer.

Example 4

An iodobromide emulsion prepared in the following manner was coated on a cellulose triacetate base. 0.8 g of a coupler, disodium 1-phenyl-3-(3,5-disulfobenzamido)-4-(n-octadecyloxyphenylazo)-5-pyrazolone, was added at room temperature under agitation to 40 ml of water. Then, to the above solution as added 5 ml of a 10 % aqueous solution of sodium hydroxide, and the reslting solution was added 40°C. into 100 ml of a 10 % aqueous solution of gelatin and 8 ml of 5 % Alkanol B. Then, 1 ml of a 7 % solution of saponin was added to the above solution and the pH was adjusted to 6.8. Then, 8 ml of a silver iodobromide was added and the mixture was agitated for 2 minutes and allowed to stand at 40°C for 30 minutes. After filtration, the liquid was coated on a support. The resulting film was exposed for 30 seconds to rays emitted from an electric lamp of 40 W disposed 1.5 m apart form the film, to thereby form a fog on the film. On the so fogged emulsion layer was coated an emulsion prepared in the following manner. 0.4 of compound (4) was added to a mixture of 0.5 ml of 2.4-di-amylphenol and 0.8 ml of dimethylformamide and dissolved thereinto by heating at 80°c. under agitation. The resulting solution was added at 40°c. to a liquid mixture of 20 ml of a 10 % solution of gelatin and 2 ml of a 5 % solution of Alkanol B. The resulting suspension was treated five times by means of a colloid mill, and the remaining dispersion was washed away from the mill with use of 8 ml of water and 2 cc of a 7 % solution of saponin. Then, 10 ml of a silver chlorobromide emulsion was added to the entire dispersion, and the mixture was agitated for 2 minutes, allowed to stand at 40°C. for 30 minutes, and then coated.

The so obtained photosensitive film for diffusion transfer was exposed to light, and then, an image-receiving layer formed by coating a gelatin liquid composed of 0.5 g of cetyltrimethyl ammonium bromide in 25 ml of a 10 % solution of gelatin was placed closedly on the above film, and then the development was conducted with use of a developer having the following Composition:

| | |
|---|---|
| sodium carbonate | 20.0 g |
| sodium hexametaphosphate | 2.0 g |
| benzyl alcohol | 10.0 g |
| 3-acetamido-4-amino-N, N-diethylaniline | 2.0 g |
| water | balance |
| TOTAL | 1 liter |

The pH of the developer was adjusted to 11. With advance of the development, a development inhibitor was formed at exposed areas and it was diffused into the lower layer of the fogged emulsion to inhibit the development at corresponding areas, but at non-exposed areas the development of the lower fogged emulsion layer was not inhibited and the color developing agent was coupled with the coupler to form a soluble magenta dye. This magenta dye was transferred in the form of an image on the image-receiving layer containing the mordant, and as result, there was obtained a positive magenta dye image excellent in sharpness.

Example 5

Coating liquids having a composition indicated below were successively coated on a cellulose triacetate base. (The amount of each ingredient was per 900 cm² of the base).

1. A red-sensitive silver iodobromide emulsion containing 440 mg of gelatin and 174 mg of silver iodobromide, in which 26.3 g of 1-hydroxy-4-(4-tert-butylphenoxy)-4-phenylazo-2-naphthanilide and 32.7 g of 1-hydroxy-N-[α-(2,4-di-tert-amylphenoxy) butyl]-2-naphthamide as couplers and 5 mg of compound (7) as the development inhibitor-releasing type compound were incorporated.

2. A gelatin intermediate layer containing 83 mg of gelatin and 3 mg of dioctyl hydroquinone.

3. A green-sensitive silver iodobromide emulsion containing 400 mg of gelatin and 243 mg of silver iodobromide, which further contained as couplers 24.5 mg of 1-(2,4,6-trichlorophenyl)-3-{3-[α-(2,4-ditert-amylphenoxy)acetamido]benzamido}-4-(4'-methoxyphenylazo)-5-pyrazolone and 24.3 mg of 1-(2,4,6-trichlorophenyl)-3-{3-[α-2,4-di-tert-amyaphenoxy)acetamido]benzamido}-5-pyrazolone and 5 mg of compound (7) as the development inhibitor-releasing type compound and 3.5 mg of dioctyl hydroquinone as an anti-stain agent.

4. A gelatin intermediate layer containing 837 mg of gelatin and 3 mg of dioctyl hydroquinone.

5. A blue-sensitive silver iodobromide containing 200 mg of gelatin and 62 mg of silver iodobromide, in which 102.5 mg of N-(P-benzoylacetamidobenzenesulfonyl)-N-(γ-phenylpropyl)-toluidine as a coupler and 1.6 mg dioctyl hydroquinone as antistain agent were further incorporated.

A comparative sample was prepared in the same manner as described above except that compound (7) was not incorporated in either the red-sensitive layer or the green-sensitive layer. Both the samples were subjected to wedge exposure and developed at 24°C. for 10 minutes with a liquid developer having the following composition:

| | |
|---|---|
| anhydrous sodium sulfite | 2.0 g |
| N-ethyl-N-β-methanesulfonamido-ethyl-3-methyl-4-aminoaniline sulfate | 5.0 g |
| sodium carbonate | 50.0 g |
| sodium bromide | 0.9 g |
| sodium hydroxide | 4.0 g |
| sodium hexametaphosphate | 0.5 g |
| benzyl alcohol | 4.0 ml |
| pure water | balance |
| TOTAL | 1 liter |

The bleach fixing treatment was conducted according to customary procedures. The sample containing compound (7) of this invention was excellent over the comparative sample with respect to the sharpness and graininess of the image, and the degree of fogging was extremely low in the sample according to this invention.

Example 6

A commercially available photographic film of the coupler incorporated type was subjected to wedge exposure and developed at 20°C. for 10 minutes with use of a develper having the following composition:

| | | |
|---|---|---|
| N-ethyl-N-β-methanesulfonamido-ethyl-3-methyl-4-aminoaniline sulfate | 5.0 | g |
| anhydrous sodium sulfite | 2.0 | g |
| benzyl alcohol | 3.8 | g |
| sodium carbonate monohydrate | 50 | g |
| potassium bromide | 1.0 | g |
| potassium hydroxide | 0.55 | g |
| compound (9) | 1.5 | g |
| water | balance | |
| TOTAL | 1 liter | |

Then, bleaching, fixing, water-washing, stabilizing and drying treatments were conducted according to customary procedures. For comparison, the same color film was treated with a color developer having the same composition as above except that compound (9) of this invention was not incorporated. It was found that in the sample according to this invention by excellent image effects the sharpness and graininess of the image were highly improved over the comparative sample and further, the sample according to invention was very clear.

What is claimed is:

1. A method for development of an imagewise exposed silver halide photosensitive material which comprises developing said material in the presence of a development inhibitor-releasing compound of the formula:

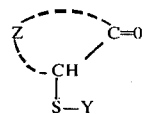

wherein Z is an atomic group necessary to form a 5 to 7 membered saturated or unsaturated carbon ring with the carbon atoms to which it is attached, said ring being unsubstituted or substituted by at least one of halogen and a member of the class consisting of alkyl, aryl, alkoxy, acyloxy, aryloxy, SY and a group forming a condensed carbon ring with said saturated or unsaturated carbon ring; Y is arylmercapto, heterocylic, thioglycollic acid, cystein and glutathione.

2. A method according to claim 1 wherein Y is taken from the class consisting of mercaptotetrazole, mercaptothiazole, mercaptooxadiazole, mercaptopiperidine, mercaptothiadiazole, mercaptotriazine, mercaptotriazole and mercaptobenzene.

3. A silver halide photosensitive material comprising a development inhibitor-releasing compound of the formula:

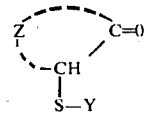

wherein Z is an atomic group necessary to form a 5 to 7 membered saturated or unsaturated carbon ring with the carbon atoms to which it is attached, said ring being unsubstituted or substituted by at least one of halogen and a member of the class consisting of alkyl, aryl, alkoxy, acyloxy, aryloxy, SY and a group forming a condensed carbon ring with said saturated or unsaturated carbon ring; Y is arylmercapto, heterocyclic, thioglycollic acid, cystein or glutathione.

4. A material according to claim 3 wherein Y is taken from the class consisting of mercaptotetrazole; mercaptothiazole, mercaptooxadiazole, mercaptopiperidine, mercaptothiadiazole, mercaptotriazine, mercaptotriazole and mercaptobenzene.

* * * * *